Figure 1:
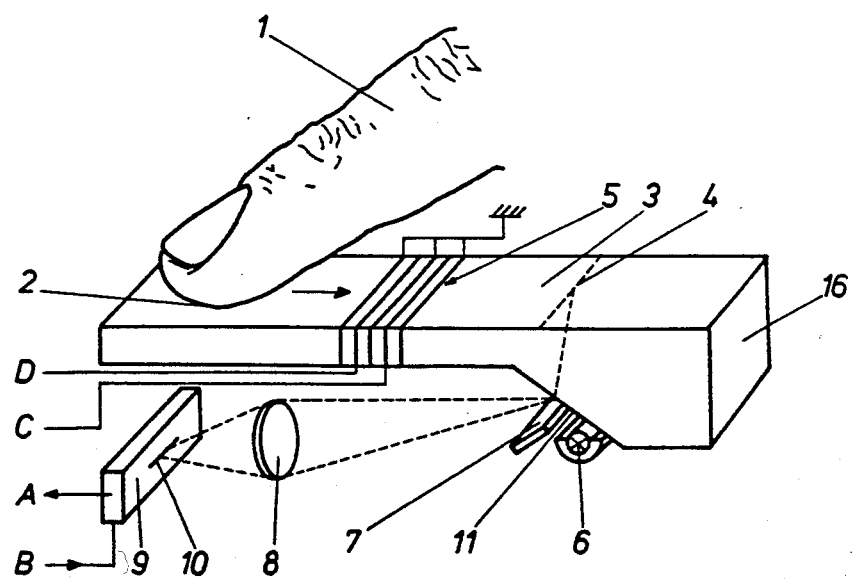

United States Patent [19]

Jensen

[11] Patent Number: 4,784,484
[45] Date of Patent: Nov. 15, 1988

[54] METHOD AND APPARATUS FOR AUTOMATIC SCANNING OF FINGERPRINTS

[75] Inventor: Palle R. Jensen, Copenhagen V, Denmark

[73] Assignee: Jydsk Telefon A/S, Aarhus, Denmark

[21] Appl. No.: 23,557

[22] PCT Filed: Apr. 28, 1986

[86] PCT No.: PCT/DK86/00044
§ 371 Date: Dec. 4, 1986
§ 102(e) Date: Dec. 4, 1986

[87] PCT Pub. No.: WO86/06266
PCT Pub. Date: Nov. 6, 1986

[30] Foreign Application Priority Data

May 2, 1985 [DK] Denmark ............................ 1984/85

[51] Int. Cl.$^4$ ............................................. G06K 9/74
[52] U.S. Cl. ....................................... 356/71; 356/72; 382/4
[58] Field of Search ................. 356/71, 72; 382/2, 4, 382/5

[56] References Cited

U.S. PATENT DOCUMENTS

| 3,639,905 | 2/1972 | Vaida et al. | 382/2 |
| 4,322,163 | 3/1982 | Schiller | 356/71 |
| 4,537,484 | 8/1985 | Fowler et al. | 382/4 |
| 4,544,267 | 10/1985 | Schiller | 356/71 |

FOREIGN PATENT DOCUMENTS

| 45913 | 2/1982 | European Pat. Off. |
| 2056472 | 6/1971 | Fed. Rep. of Germany |
| 321110 | 2/1970 | Sweden |

Primary Examiner—F. L. Evans
Attorney, Agent, or Firm—Merchant, Gould, Smith, Edell, Welter & Schmidt

[57] ABSTRACT

An apparatus for automatic scanning of a fingerprint by optical scanning of the fingerprint side (2) of a finger (1) comprises a scanning surface (3) with a measuring means (5) for the rate of movement of the finger in relation to the scanning surface, and with a scanning area (4), a lighting means (6), an optical system (7,8) and an electrical/optical scanning means (9) giving an electrical signal (A) as a function of the fingerprint when the finger is moved in contact with the scanning surface (3) in the direction of the arrow.

The scanning is undertaken by line scanning along the scanning line (4) in that the scanning line is imaged onto the active part of the scanning means (9). The active part consists for example of a number of substantially punctiform photodiodes (10) which are coupled in the electrical circuit and receives control signals (B) so that the photodiodes are scanned successively.

10 Claims, 2 Drawing Sheets

METHOD AND APPARATUS FOR AUTOMATIC SCANNING OF FINGERPRINTS

There are known various methods for optical scanning of the fingerprint side of a finger for ascertaining the identity of a person or for identifying the characteristic papillary pattern of a finger. The scanning may take place manually and the papillary pattern may be characterised by means of one of the known systems whereof some are digital so that the pattern characteristics may be machine processed as soon as the characterisation has been completed. Manual scanning, however, is highly time-consuming because a fingerprint readily comprises 25 characteristic details whereof at least 6-10 details will often have to be characterised in order to achieve positive identification.

There has therefore been developed various apparatuses for optical scanning of the fingerprint side of a finger. These apparatuses have a movable optical means which scans the fingerprint side. Mechanically movable means are difficult to design so that they will not take up too much space and such apparatuses moreover require regular maintenance.

The object of the invention is to provide a method and an apparatus for optical/electrical scanning of the fingerprint side of a finger without using any mechanically movable means so that there is obtained an apparatus which will not require maintenance. It is moreover an object to provide an apparatus which is rather small so that it can be built into existing apparatuses such as telephone apparatus, entrance control apparatus and the like.

Instead of mechanically scanning the fingerprint side, it is according to the invention the finger which is moved during an optical/electrical scanning where simultaneously with or immediately before the scanning the rate of movement of the finger is measured. The mechanical movements in the known apparatuses have thereby been transferred into a modest finger movement where in stead of placing the finger on or in a scanning means, the finger is slid on a scanning surface, whereby the fingerprint side is scanned and there is obtained an electrical signal representing the fingerprint which signal can be processed in the usual manner in electrical apparatuses for example for comparaison with stored information.

It is sufficient to make the scanning surface transparent at the place of scanning. The points along the scanning line where the finger touches the surface (the ridges of the fingerprint) will reflect the light differently from the points where the finger does not touch the surface. By scanning the passing finger line by line there is obtained a complete scanning of the fingerprint.

Certainty of identification or recognition is achieved in that the use of copied prints of fingers or the use of a false finger such as a plastic or rubber cast is thereby excluded. By proceeding as disclosed it is simply checked whether it is a true finger or not.

By a uniform friction between the finger and the scanning surface it is possible in a simple manner electrically to synchronise or scale the line scanning with the rate of movement which will be sufficiently constant during the scanning. The rate measuring is thus used for synchronising or scaling the scanning.

By measuring the skin resistance as disclosed there is obtained a sufficiently accurate measuring to determine whether it is a genuine finger or not.

It is sufficient to make the scanning area transparent by the scanning line. If, for example, a scanning surface made of plastics, for example glass or synthetic materials such as acrylic plastics is used, the entire surface except the scanning area itself may be coated by a black coating such as black paint or the like so that undesirable light or undesirable reflections are avoided. There is thus obtained an apparatus that is insensitive to changes in light strength etc. in the surroundings where the apparatus has been mounted.

There is thus obtained a simple apparatus where the purely physical design may be changed in many different ways, for example dependent on where the apparatus is to be used or mounted.

The functioning of the apparatus and certainty of correct measuring are further increased by designing the apparatus as disclosed. This will not, however, substantially increase the complexity or power consumption of the apparatus.

The apparatus can be divided in two parts, one part where the scanning is done, and another part, the electrical part, from where the scanning is monitored and controlled. The two parts may without any practical problems be placed apart.

It is obvious that a method and an apparatus according to the invention may be used for many different purposes, but has preferably been developed for use in connection with entrance control.

Figure 2:
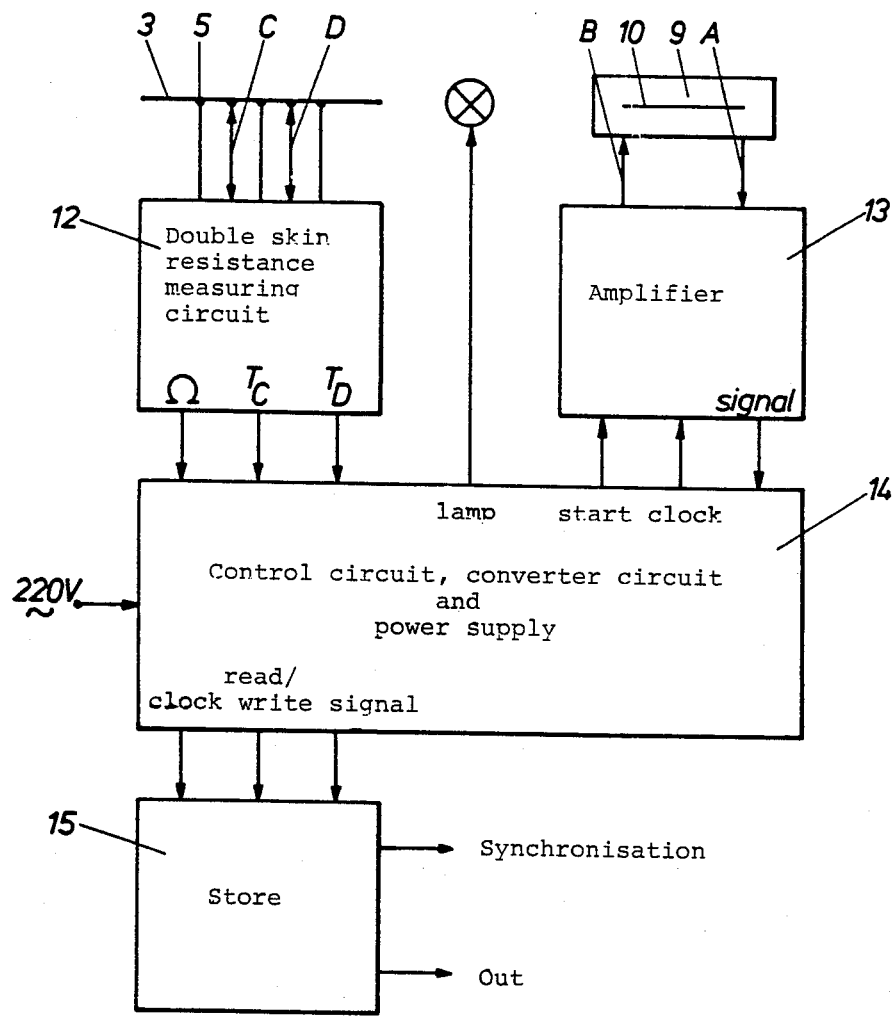

The invention will be further explained in the following with reference to the drawing showing an embodiment of the invention wherein FIG. 1 shows the scanning system itself, and FIG. 2 shows the electrical circuit therefor.

In the drawing reference numeral 1 is a finger, the fingerprint side 2 of which is to be scanned. The finger is moved in contact with a scanning surface 3 on a part 16 of an apparatus which part may for example be a moulded acrylic block or a similar transparent material. In the scanning surface 3 there is arranged a measuring means 5 for skin resistance and finger rate of movement and there is moreover shown a scanning area 4 in the form of a scanning line. The scanning surface 3 with the measuring means 5 is designed so as to give all over the surface a substantially uniform friction against the finter movement so that without problems it is possible to move the finger at the same constant rate across the measuring means 5 and the scanning line 4. The measuring means 5 consists for example of five mutually separated measuring wires made of electrically conducting material embedded in the surface. The centre wire and the two outer wires are connected to each other and are used as reference, for example frame connected, whereas the two remaining wires C and D are connected to the measuring circuit shown in FIG. 2. The rate of the finger is measured by registering the points of time $T_C$ and $T_D$ where the finger 1 loses contact with the second and the fourth wire, respectively, in the direction of movement.

In the shown and explained example the measuring means 5 has five measuring wires. It is obvious that it is possible to use some other number of measuring wires—the entire surface 3 may if so desired be covered by measuring wires—dependent on the measuring method etc.

Under the apparatus part 16 there is arranged an elongate lighting means 6, for example an elongate lamp, a dense row of light diodes or some other form of elongate light source. The lighting means 6 is placed perpendicularly to the direction of movement of the finger and is provided with a reflector or a slit-shaped shutter so that substantially all light is directed towards the scanning area 4. The lighting means 6 may be mounted next to the apparatus part 16 as shown in FIG. 1, but may also be mounted inside the apparatus part 16, for example in a cylindrical cross bore. Next to a light pass surface 11 there is provided a mirror 7, for example a surface mirror throwing reflected light from the entire scanning area 4 onto the active part 10 of an optical-/electrical scanning means 9 which part 10 is for example a linear photoarray with for example 256 punctiform photocells. The line 4 is imaged onto the linear photoarray 10 by means of an optical system that may comprise one or more lenses 8. The optical/electrical means 9 receives control signals through a wire B in such a manner that only one photocell at a time will give an electrical signal through the wire A representing the light intensity by which the cell is influenced. Through wire A there is thus obtained an electrical analog signal representing reflected light from the line 4, i.e. a line scanning of the contact print against the scanning surface 3 of the print side 2 of the finger.

The rate of movement of the finger 1 measured with the measuring means 5 is used for synchronising or scaling the scanning.

In order to avoid false reflections and to be capable of using as weak a lighting means 6 as possible, the entire apparatus part 16 has been painted dull black, except on the scanning area 4 and on the light pass surface 11.

By adjusting the mirror 7 it is possible to move the scanning area 4, for example in such a manner that it is placed quite close to the rate measuring means 5. If desired, the scanning line 4 may be placed between two of the measuring wires, for example between the two last wires in the direction of movement of the finger.

FIG. 2 of the drawing shows a schematic block diagram of the electrical circuit. At the left top the scanning surface 3 with the measuring means 5 and the two measuring wires C and D are shown. A 10 kHz square voltage may for example be applied to the wires C and D so that noise and mains hum problems are avoided. The wires C and D are connected to each its bridge circuit and the finger contact is detectd when the bridge is brought off balance when the finger touches the wire. The points of time $T_C$ and $T_D$ are measured when the finger leaves the respective wire and the time difference is used as an expression of the rate of movement of the finger. At the same time the circuit 12 measures the skin resistance twice i.e. between wires C and D and the other three connected wires, respectively. The result of the measurement of the skin impedance or the skin resistance and the measured points of time $T_C$ and $T_D$ is directed to a control and converter circuit 14 which also contains the power supply to the various circuits and the lighting means 6.

The scanning means 9 is via an amplifier 13 connected to the control and converter circuit 14 which inter alia by means of the impulses received from a clock generator undertakes the required controlling, signal processing and digitalisation of the measurement results from the photo array 10 and sends the digital measurement results to a binary store 15 such as a 256×256×1 bit store which may exactly hold one complete fingerprint. It is obvious to a person skilled in the art that other sizes and forms of store circuits may be used. From the store 15 the digitalised fingerprint may be transmitted for data processing together with any required synchronisation signal.

The data processin itself of the stored fingerprint does not form part of the invention and will therefore not be further described.

It is obvious to a person skilled in the art that the electrical circuit shown in FIG. 2 may be designed and built up in a great number of different ways and that the circuit may moreover be constructed by using generally known circuits while obtaining the desired function.

What is claimed is:

1. Method for automatic scanning of fingerprints by optical scanning of the fingerprint side of a finger, characterised in that the finger is moved along a scanning surface while measuring the rate of movement of the finger in relation to the scanning surface and in such a manner that by contact between the finger and surface there is formed an optical papillary pattern corresponding to a fingerprint whereupon the pattern is scanned when passing a scanning area and is converted into an electrical signal.

2. Method according to claim 1, characterised in that the scanning surface is transparent in the scanning area and the passing papillary pattern is scanned line by line perpendicularly to the direction of movement.

3. Method according to claim 1, characterised in that the skin resistance of the finger is measured substantially at the same time while measuring the rate of movement.

4. Method according to claim 3, characterised in that the entire scanning surface is designed so as to give substantially the same friction against the finger and that the skin resistance and the rate of movement are measured immediately before or simultaneously with the scanning of the fingerprint and that there is formed no electrical signal corresponding to the finger print if the skin resistance and/or the rate of movement lie(s) outside pre-determined ranges.

5. Method according to claim 3, characterised in that the skin resistance is measured by an impedance measuring device using alternating current.

6. An apparatus for automatic scanning of fingerprints by optical scanning of the fingerprint side of a finger comprising: a scanning surface having means for measuring the rate of movement of the finger across said surface, said scanning surface having a scanning area thereon which includes scanning means for illuminating said area and means for detecting illumination reflected from said area to generate an electrical signal as a function of said reflected light.

7. Apparatus according to claim 6, characterised in that the scanning surface is transparent in the scanning area and is rectilinear and transverse to the direction of movement of the finger and including means to scan, line by line, the fingerprint as the finger passes the area and wherein said area has substantially uniform surface friction.

8. Apparatus according to claim 6, characterised in that the scanning means includes an elongate light source provided, with a reflector and further includes focusing means and deflector means whereby the scanning area is imaged onto the scanning means, said scanning means further including an array of substantially punctiform photodiodes and an electrical circuit which supplies control signals to successively scan said photodiodes.

9. Apparatus according to claim 6, characterised in that the measuring means (5) is furthermore provided with conductor means (c, D) for measuring the skin resistance of the fingerprint side (2).

10. Apparatus according to claim 6, characterised in that the measuring means consists of a number of electrical conductors placed apart and arranged transverse to the direction of movement in the surface of the scanning surface where between some of the conductors there is applied an alternating voltage for determining the impedance of the skin and a voltage for determining the rate of movement of the finger in that the points of time are scanned when the finger loses electrical contact with the conductors and the time difference is used for determining the rate of movement.

* * * * *

UNITED STATES PATENT AND TRADEMARK OFFICE
CERTIFICATE OF CORRECTION

PATENT NO. : 4,784,484

DATED : November 15, 1988

INVENTOR(S) : Pelle R. Jensen

It is certified that error appears in the above-identified patent and that said Letters Patent is hereby corrected as shown below:

Column 1, line 60, insert -- There is moreover obtained increased safety against undue entering or wrong indenti- --.

Column 4, line 3, "procession" should be --processing--;

Column 5, line 1, small "c" should be capital --C--.

Signed and Sealed this

Thirtieth Day of May, 1989

Attest:

DONALD J. QUIGG

Attesting Officer

Commissioner of Patents and Trademarks